(12) United States Patent
Tanaka et al.

(10) Patent No.: US 6,878,853 B2
(45) Date of Patent: Apr. 12, 2005

US006878853B2

(54) PROCESS FOR PREPARING DIHALOGENATED ADAMANTANES

(75) Inventors: Norihiro Tanaka, Shunan (JP); Masao Yamaguchi, Shunan (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 10/493,892

(22) PCT Filed: Nov. 11, 2002

(86) PCT No.: PCT/JP02/11718

§ 371 (c)(1),
(2), (4) Date: Apr. 26, 2004

(87) PCT Pub. No.: WO03/042139

PCT Pub. Date: May 22, 2003

(65) Prior Publication Data

US 2004/0260127 A1 Dec. 23, 2004

(51) Int. Cl.[7] .......................................... C07C 570/262
(52) U.S. Cl. ........................ 570/261; 570/123; 570/176
(58) Field of Search ................................ 570/261, 123, 570/176

(56) References Cited

FOREIGN PATENT DOCUMENTS

| JP | 2138139 | 5/1990 | ........... C07C/23/38 |
| JP | 2002-145809 | 5/2002 | ........... C07C/17/10 |
| RU | 2 125 551 C1 | 12/1996 | |

OTHER PUBLICATIONS

Rakhimov, A, I. et al.; Politekh. Inst., Volgograd, USSR. Zhurnal Organicheskoi Khimii (1986), 22(3), 540–2.

Chalais, Stephane et al., "Direct Clay–Catalyzed Friedel-Crafts Arylation and Chlorination of the Hydrocarbon Adamantane", Institut de Chimie Organique et de Biochimie, Universite de Liege, Sart–Tilman, B–4000 Liege, Helvetica Chimica Acta, vol. 68 (1985) pp. 1196–1203.

G.A. Tolstikov, et al., "New Method of Polyhaloadamantane Synthesis", Institute of Chemistry, Bashkirian Branch of the Academy of Sciences of the USSR, Tetrahedron Letters No. 31, pp. 3191–3192, 1972. Pentagon Press.

R. Jalal and R. Gallo, "Improved Synthesis of 1–Chloroadamantane by Hydride Transfer Induced by Tertiarybutylchloride", Synthetic Communications, 19(9&10), pp. 1697–1704 (1989).

G.A. Tolstikov, et al., New Method of Polyhaloadamantane Synthesis, 1972, pp. 3191–3192, Tetrahedron Letters No. 31, Pergamon Press.

*Primary Examiner*—Samuel Barts
*Assistant Examiner*—Lansana Nyalley
(74) *Attorney, Agent, or Firm*—Norris McLaughlin & Marcus PA

(57) ABSTRACT

This invention discloses a process for preparing a dihalogenated adamantane by reacting an adamantane optionally substituted with alkyl at 1-position with a halosulfonic acid, comprising the first stage of monohalogenation conducted at −5 to 15° C. and then the second stage of dihalogenation conducted at 17 to 35° C., preferably in the absence of an organic solvent.

5 Claims, No Drawings

PROCESS FOR PREPARING DIHALOGENATED ADAMANTANES

TECHNICAL FIELD

This invention relates to a process for preparing a dihalogenated adamantane useful as a raw material for producing a functional or electronic material.

BACKGROUND OF THE INVENTION

Adamantane derivatives have been expected to be used as a raw material for producing a high-function material such as a highly heat resistance polymer material or an electronic material such as a semiconductor resist because they exhibit excellent heat resistance and transparency. Among others, dihalogenated adamantanes are important as raw materials for preparing a variety of adamantane derivatives having bifunctional groups.

A variety of halogenated adamantanes have been prepared from adamantane, for example, by reacting adamantane with a haloalkane in the presence of an aluminum halide [Synth. Commun., 19(9–10), 1697–1704 (1989)] or by reacting adamantane with a haloalkane in the presence of a cobalt salt [RU 2125551 (1999)]. These processes, however, generally provide a mixture of mono-, di-, and/or tri-halogenated adamantanes. Furthermore, such a mixture generally contains a monohalogenated adamantane as a main product, with a lower yield of a dihalogenated adamantane.

Tetrahedron Letters 31, 3191–3192 (1972) has disclosed a process for selectively preparing a dihalogenated adamantane, where adamantane is mixed and reacted with a halosulfonic acid at 20° C. In this synthetic method, the reaction, however, sharply proceeds during the initial stage. Thus, when using a sufficient amount of a halosulfonic acid in attempting to improve an yield, the reaction tends to excessively proceed, leading to formation of trihalogenated derivatives. The above preparation process is, therefore, improper with respect to an yield of a dihalogenated adamantane. For example, when adamantane and chlorosulfonic acid are charged in the molar ratio of 1:8 and reacted for about 10 hours, an yield of 1,3-dichloroadamantane is 80% or less as determined by gas chromatography.

For selectively preparing a dihalogenated adamantane, Zh. Org. Khim., 22 (3), 540–542 (1986) and Helv. Chim. Acta, 68 (5), 1196–1203 (1985) have used an iron halide. However, when preparing a dihalogenated adamantane using a metal compound, a dihalogenated adamantane prepared may be frequently contaminated with a metal. In an electronic device, contamination with a trace amount of a metal may be deleterious to its performance. A dihalogenated adamantane prepared according the process cannot be, therefore, used for manufacturing such an electronic device. Further purification of a dihalogenated adamantane contaminated with a metal is cumbersome, leading to increase in a cost.

The above preparation process may provide a dihalogenated adamantane in a relatively higher yield, but the dihalogenated adamantane thus prepared inevitably contains several percents of a monohalogenated adamantane, which is an intermediate. For providing the highly pure dihalogenated adamantane, separation of the monohalogenated adamantane is essential. These compounds, however, exhibit very similar chemical properties, and thus cannot be separated by a common and convenient method. They are, therefore, generally separated by chromatography. However, chromatographic separation can deal with a small amount in a single run and takes much time, leading to lower overall productivity. Thus, the procedure is not suitable for production in a large scale.

SUMMARY OF THE INVENTION

We have intensely attempted to solve the above problems and have finally found that these problems can be solved by reacting adamantane and a halosulfonic acid under a particular temperature condition, achieving this invention.

An objective of this invention is, therefore, to provide a process for preparing a highly pure dihalogenated adamantane in a high yield under mild conditions without using a metal or metal salt.

This invention provides a process for preparing a dihalogenated adamantane by reacting an adamantine which is optionally substituted with alkyl at 1-position with a halosulfonic acid, comprising the first stage of monohalogenation conducted at −5 to 15° C. and then the second stage of dihalogenation conducted at 17 to 35° C.

DETAILED DESCRIPTION OF THE INVENTION

In this invention, the adamantane as a raw material is generally unsubstituted, but may be optionally substituted with alkyl at 1-position. The alkyl is preferably linear alkyl having 1 to 4 carbon atoms such as methyl, ethyl and propyl, particularly preferably methyl.

The halosulfonic acid used in this invention is a compound represented by:

$$XSO_3H$$

wherein X represents halogen. Examples of halogen includes fluorine, chlorine, bromine and iodine. Specifically, the halosulfonic acid may be chlorosulfonic acid, bromosulfonic acid, iodosulfonic acid or the like. In the light of availability, chlorosulfonic acid is particularly preferable.

In this invention, the adamantane optionally substituted with alkyl at 1-position (hereinafter, also referred to as "adamantane compound") is reacted with a halosulfonic acid to give a dihalogenated adamantane.

When the adamantane compound is unsubstituted, a dihalogenated adamantane as a main product is a 1,3-dihalogenated adamantane represented by formula (1):

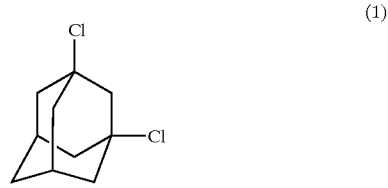

(1)

Generally, in addition to the 1,3-dihalogenated adamantane, other dihalogenated adamantanes may be formed in a small amount.

When the adamantane compound is substituted with alkyl at 1-position, a dihalogenated adamantane as a main product is 1-alkyl-3,5-dihalogenated adamantane represented by formula (2):

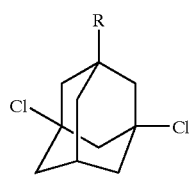

(2)

wherein R represents linear alkyl having 1 to 4 carbon atoms.

Generally, in addition to the 1-alkyl-3,5-dihalogenated adamantane, other dihalogenated adamantanes may be formed in a small amount.

In the synthetic reaction, there are no limitations to charge ratios for an adamantane compound and a halosulfonic acid. However, since an extremely small rate of the halosulfonic acid may lead to inadequate reaction, a molar ratio of the halosulfonic acid is preferably two or more to the adamantane compound. As described later, a molar ratio of the halosulfonic acid to the adamantane compound is 5 to 15, most preferably 8 to 12 for allowing the halosulfonic acid to sufficiently function as a reaction solvent and improving an yield when conducting the reaction without using an organic solvent.

There are no limitations to a procedure for mixing the adamantane compound and the halosulfonic acid. Preferably, the halosulfonic acid is added dropwise to the adamantane or a solution of the adamantane in an organic solvent.

This invention is primarily characterized in that in the reaction between the above adamantane compound and a halosulfonic acid, the first monohalogenation is conducted at −5 to 15° C. and then the second dihalogenation is conducted at 17 to 35° C. Such a characteristic two-stage reaction at different temperatures can reduce the amount of byproducts such as trihalogenated adamantanes to give more selectively a desired dihalogenated adamantane.

Generally in the reaction between an adamantane compound and a halosulfonic acid, the adamantane compound is first monohalogenated (hereinafter, the reaction is also referred to as a "monohalogenation"). Then, halogenation proceeds to form a dihalogenated derivative (hereinafter, the reaction is also referred to as a "dihalogenation"). Further halogenation may proceed to give tri- and tetra-halogenated derivatives in sequence. When the reaction is conducted maintaining a reaction temperature in the range of −5 to 15° C., monohalogenation proceeds, while under the temperature condition, a further halogenation of a monohalogenated derivative to a dihalogenated derivative little proceeds. Dihalogenation rapidly proceeds at a reaction temperature of more than 17° C.

If the reaction temperature is 17° C. or higher from the initial stage of the reaction, the reaction rapidly proceeds from the initial stage to give a dihalogenated derivative and finally halogenation tends to rush to provide trihalogenated derivatives. Thus, under the temperature condition, trihalogenated derivatives are formed in a significant amount, resulting in a lower yield of the dihalogenated adamantane.

In contrast, when a reaction temperature is set in two steps such that the reaction proceeds under mild conditions in the initial stage, a reaction further forming a trihalogenated derivative after forming of the dihalogenated derivative little proceeds even when a temperature is set to 17° C. or higher in the subsequent second stage. As a result, the dihalogenated adamantane can be formed in a higher yield.

If a reaction temperature is lower than 5° C., monohalogenation does not sufficiently proceed. Thus, a reaction temperature in the first stage is preferably 5 to 15° C. If a reaction temperature is lower than −5° C., monohalogenation little proceeds.

During the step of mixing an adamantane compound with a halosulfonic acid, a liquid temperature is preferably maintained at 5° C. or lower to avoid a runaway reaction.

The monohalogenation in the first stage is continued until the charged adamantane compound is substantially monohalogenated. A reaction time is generally at least 30 min, preferably 1 to 3 hours.

After the first monohalogenation stage, the second-stage dihalogenation is conducted. A reaction temperature in the second stage is suitably 17 to 25° C. in the light of providing a dihalogenated adamantane in a particularly higher yield. If the reaction temperature in the second stage is higher than 35° C., trihalogenation of the dihalogenated adamantane tends to considerably proceed.

It is necessary to continue the second reaction until dihalogenation adequately proceeds. However, an excessively longer reaction time may lead to gradual formation of trihalogenated adamantanes. Thus, a reaction time is preferably 1 to 24 hours, particularly 3 to 8 hours.

If desired, a reaction temperature may be varied in multiple steps within the temperature range defined above in each of the first and the second stages. A reaction pressure in each reaction stage is generally, but not limited to, an ambient pressure.

The above two-stage reaction may be conducted in the absence or presence of an organic solvent. However, the reaction is particularly preferably conducted in the absence of an organic solvent, where a halosulfonic acid may be also used as a solvent.

An adamantane compound or dihalogenated adamantane is little soluble in a halosulfonic acid whereas a monohalogenated adamantane is significantly soluble in a halosulfonic acid. A halosulfonic acid exhibits such a specific dissolution property. Therefore, without an organic solvent, a halosulfonic acid as a reaction reagent may be also used as a reaction solvent to efficiently utilize the above specific dissolution property of the halosulfonic acid. Thus, as described below, a dihalogenated adamantane can be selectively provided in a higher purity.

Specifically, on charging an adamantane compound and a halosulfonic acid, a reaction mixture is initially a suspension in which the adamantane compound is suspended. As the first stage reaction proceeds over time to produce a monohalogenated adamantane, the reaction is changed into a clear homogeneous solution because the product is soluble in the halosulfonic acid. Then, the monohalogenated adamantane thus formed is smoothly subjected to further halogenation in the halosulfonic acid to give a dihalogenated derivative. The dihalogenated adamantane thus formed is, however, substantially insoluble in the halosulfonic acid as described above, so that most of the product precipitates. As a result, the reaction mixture again becomes a suspension. When the dihalogenated adamantane have thus precipitated in the halosulfonic acid, the dihalogenated adamantane becomes significantly unreactive to the halosulfonic acid. Consequently, formation of trihalogenated adamantanes as byproducts can be substantially reduced in the second stage reaction.

In the first stage reaction, as monohalogenation proceeds, a reaction mixture changes from a suspension to a homogeneous solution. Such change allows the endpoint of the first stage reaction to be visually determined with ease. Thus, it can eliminate the problems that while the first stage reaction has not adequately proceeded, the second stage reaction is initiated, leading to increase in an amount of trihalogenated adamantanes formed and that the first stage reaction is continued for an unnecessarily longer time.

Precipitation of the dihalogenated adamantane formed during the second stage reaction is very advantageous to isolation of the desired product. Specifically, when producing a crude dihalogenated adamantane by reacting an adamantane compound with a halosulfonic acid as usual, separation of the desired dihalogenated adamantane from a monohalogenated adamantane having physico-chemical properties similar to those of the dihalogenated adamantane is generally conducted by a cumbersome purification procedure such as chromatography.

In contrast, when the reaction is conducted in the absence of an organic solvent to produce a desired dihalogenated adamantane suspended in the reaction as is in this invention, trihalogenated adamantanes are little formed as described above. Furthermore, the unreacted monohalogenated adamantane is dissolved in the reaction mixture. Therefore, the reaction mixture can be filtered to easily isolate the highly pure dihalogenated adamantane.

The filtration is preferably conducted under nitrogen atmosphere. If a temperature of the reaction during filtration is higher than the upper limit of the temperature range in the second stage reaction, the conversion of the dihalogenated adamantane into a trihalogenated adamantane may proceed, and a solubility of the dihalogenated adamantane may be increased, leading to reduction in an yield. It is, therefore, preferable to filtrate the reaction mixture within the temperature range of the second stage reaction.

The precipitate of the dihalogenated adamantane thus obtained may be further purified by an appropriate method such as washing with water, extracted with a solvent and crystallization.

When the reaction is conducted in an organic solvent, the organic solvent may be any of those which are unreactive to the halosulfonic acid; for example, chlorinated solvents such as dichloromethane and 1,2-dichloroethane.

The amount of the organic solvent is not limited as long as it can adequately dissolve reactants and does not significantly reduce a batch yield. Specifically, the amount is preferably 5 to 20 parts by weight to one part of the adamantane compound.

In this reaction using an organic solvent, a dihalogenated adamantane produced is generally dissolved in a reaction mixture at the end of the second stage reaction. The dihalogenated adamantane can be isolated from the reaction mixture, for example, by adding ice-water to the reaction mixture to decompose the halosulfonic acid, separating the organic solvent layer containing the dihalogenated adamantane from the aqueous layer, washing the organic layer, evaporating the organic layer to give a residue, which is then dried and crystallized.

An equipment used in the reaction according to this invention preferably has a structure in which contact of the reaction system with the air can be avoided. Such a structure can prevent generation of an acid gas due to decomposition of the halosulfonic acid by its reaction with moisture. Before conducting the reaction, the atmosphere inside of the equipment is sufficiently replaced with an inert gas such as nitrogen and dried. It is preferable to close the system or continuously feed an inert gas such as nitrogen into the system during the reaction.

The process of this invention is based on a two-stage reaction under controlling certain temperature, so that a dihalogenated adamantane can be prepared in a higher yield under mild conditions, without using a metal or metal salt which may contaminate the product to cause various problems. Furthermore, when the reaction is conducted in the absence of a solvent, difference in a solubility between a dihalogenated adamantane and a monohalogenated adamantane in a halosulfonic acid can be utilized to easily isolate and purify the dihalogenated adamantane with a higher yield.

A dihalogenated adamantane prepared by the process of this invention may be, for example, hydrolyzed or ammonolyzed into an adamantane diol or diaminoadamantane, respectively, which can be beneficially used as a raw material for a functional material such as a heat resistant polymer or an electronic material such as a resist.

EXAMPLES

This invention will be more specifically described with reference to, but not limited to, Examples.

Example 1

In a 100 mL three-necked flask was placed 5.0 g of adamantane (0.037 mol) and then the inside of the flask was dried by purging with nitrogen gas. Under the nitrogen stream, the flask was cooled to an internal temperature of 0° C., and then 43.1 g of chlorosulfonic acid (0.37 mol) was added dropwise. The reaction mixture as a suspension was warmed to 10° C. to initiate the first stage reaction with effervescence. The reaction was maintained at the temperature until effervescence ceased. After 2 hours, the reaction became a clear and homogeneous solution.

The reaction mixture was warmed to 20° C. to initiate the second stage reaction with mild effervescence again. The reaction was maintained under the conditions for 5 hours. The reaction mixture as a suspension was filtrated under a nitrogen atmosphere. The solid thus obtained was poured into ice-water and extracted with chloroform. After replacing the solvent with hexane, the organic layer was filtrated. After adding charcoal, the filtrate was again filtrated. After evaporation, the residue was dried to give 7.0 g of a white solid (yield: 93%).

The while solid contained 1,3-dichloroadamantane in a purity of 94% as determined by gas chromatography.

Comparative Example 1

Halogenation was conducted as described in Example 1, except that chlorosulfonic acid was added to 5.0 g of adamantane (0.037 mol) at 20° C. and the reaction was continued at the temperature for 7 hours, to give 5.6 g of a white solid (yield: 75%).

The analysis results indicated that the white solid contained 1,3-dichloroadamantane in a purity of 78%.

Comparative Example 2

As described in Example 1, chlorosulfonic acid was added dropwise to 5.0 g of adamantane (0.037 mol) at 10° C. and the reaction was continued for 2 hours. The reaction mixture became a clear and homogeneous solution. Then, the reaction mixture was warmed to 40° C. and the reaction was continued for 5 hours. The reaction was then processed as described in Example 1 to give 5.3 g of a white solid (yield: 71%). The analysis results indicated that the white solid contained 1,3-dichloroadamantane in a purity of 80%.

Example 2

Halogenation was conducted as described in Example 1, except that a reaction temperature during the first stage was 15° C. and one hour was taken for making the reaction mixture clear and homogeneous, to give 6.7 g of a white solid (yield: 89%).

The analysis results indicated that the white solid contained 1,3-dichloroadamantane in a purity of 91%.

Example 3

Halogenation was conducted as described in Example 1, except that in the second stage, a reaction temperature was 30° C. and the reaction time was 3 hours, to give 6.8 g of a white solid (yield: 90%).

The analysis results indicated that the white solid contained 1,3-dichloroadamantane in a purity of 89%.

Example 4

Halogenation was conducted as described in Example 1, except that the amount of chlorosulfonic acid was 25.9 g (0.22 mol) and a reaction time of the second stage was 8 hours, to give 6.5 g of a white solid (yield: 86%).

The analysis results indicated that the white solid contained 1,3-dichloroadamantane in a purity of 92%.

Example 5

Halogenation was conducted as described in Example 1, except substituting 5.5 g of 1-methyladamantane (0.037 mol) for 5.0 g of adamantane (0.037 mol), to give 7.2 g of a white solid (yield: 90%).

The analysis results indicated that the white solid contained 1-methyl-3,5-dichloroadamantane in a purity of 90%.

Example 6

Halogenation was conducted as described in Example 1, except substituting 59.6 g of bromosulfonic acid (0.37 mol) for 43 g of chlorosulfonic acid (0.37 mol), to give 9.5 g of a white solid (yield: 88%).

The analysis results indicated that the white solid contained 1,3-dibromoadamantane in a purity of 92%.

Example 7

In a 100 mL three-necked flask was placed 5.0 g of adamantane (0.037 mol) and then the inside of the flask was dried by purging with nitrogen gas. Under the nitrogen stream, 50 mL of dehydrated dichloromethane was added and the mixture was cooled to 0° C. To the mixture was then added dropwise 43.1 g of chlorosulfonic acid (0.37 mol). The reaction as a suspension was warmed to 10° C. to initiate the first stage reaction with effervescence, and the reaction was continued at 10° C. for 2 hours.

The reaction mixture was warmed to 20° C. to initiate the second stage reaction with mild effervescence again, and the reaction was continued for 5 hours. The reaction solution was poured into ice-water, and the mixture was stirred until the mixture was warmed to room temperature. The mixture was extracted with 100 mL of dichloromethane twice. The combined extracts were washed with water and evaporated. The residue was dissolved in hexane and the solution was filtrated. After adding charcoal, the solution was again filtrated and the solvent was evaporated. The residue was dried to give 6.8 g of a white solid (yield: 90%).

The white solid contained 1,3-dichloroadamantane in a purity of 89% as determined by gas chromatography.

Comparative Example 3

In a 100 mL three-necked flask was placed 5.0 g of adamantane (0.037 mol) and then the inside of the flask was dried by purging with nitrogen gas. Under the nitrogen stream, into the three-necked flask were added 50 mL of 2-chloro-2-methylpropane and 1.0 g of aluminum chloride, and then the mixture was refluxed for 8 hours. The reaction solution was poured into ice-water, and the mixture was stirred until it was warmed to room temperature. The solution was filtrated and extracted with chloroform twice. The combined extracts were washed with water once and evaporated. The residue was dissolved in hexane and the solution was filtrated. After adding charcoal, the solution was again filtrated. The solvent was evaporated and the residue was dried to give 5.3 g of a white solid.

The white solid contained 90% of 1-chloroadamantane and 5% of 1,3-dichloroadamantane as determined by gas chromatography.

What is claimed is:

1. A process for preparing a dihalogenated adamantane by reacting an adamantane optionally substituted with alkyl at 1-position with a halosulfonic acid, comprising the first stage of monohalogenation conducted at −5 to 15° C. and then the second stage of dihalogenation conducted at 17 to 35° C.

2. The process for preparing a dihalogenated adamantane as claimed in claim 1 wherein the first stage of monohalogenation and the second stage of dihalogenation are conducted in the absence of an organic solvent.

3. The process for preparing a dihalogenated adamantane as claimed in claim 2 wherein the first stage of monohalogenation is continued until a reaction mixture becomes a homogenous solution.

4. The process for preparing a dihalogenated adamantane as claimed in claim 2 wherein the reaction mixture after the second stage of dihalogenation is filtrated to isolate the dihalogenated adamantane.

5. The process for preparing a dihalogenated adamantane as claimed in claim 1 wherein the halosulfonic acid is charged in a molar ratio of 5 to 15 to the adamantane optionally substituted with alkyl at 1-position.

* * * * *